(12) United States Patent
Sagara et al.

(10) Patent No.: US 8,883,777 B2
(45) Date of Patent: Nov. 11, 2014

(54) COMPOSITIONS CONTROLLING PH RANGE OF RELEASE AND/OR RELEASE RATE

(75) Inventors: Kazuyoshi Sagara, Tokyo (JP); Tomoyuki Omura, Tokyo (JP); Hirofumi Samemoto, Tokyo (JP); Hirotsugu Komatsu, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 0 days.

(21) Appl. No.: 13/448,538

(22) Filed: Apr. 17, 2012

(65) Prior Publication Data

US 2012/0202798 A1    Aug. 9, 2012

Related U.S. Application Data

(60) Division of application No. 12/222,213, filed on Aug. 5, 2008, now abandoned, which is a continuation of application No. 10/319,568, filed on Dec. 16, 2002, now abandoned, which is a continuation-in-part of application No. PCT/JP01/05151, filed on Jun. 15, 2001.

(30) Foreign Application Priority Data

Jun. 16, 2000    (JP) .................................. 2000-182293

(51) Int. Cl.
| | | |
|---|---|---|
| *A61K 31/551* | (2006.01) | |
| *A61K 9/16* | (2006.01) | |
| *A61K 31/5517* | (2006.01) | |
| *A61K 9/14* | (2006.01) | |
| *A61K 9/20* | (2006.01) | |

(52) U.S. Cl.
CPC ............ *A61K 9/1635* (2013.01); *A61K 9/1676* (2013.01); *A61K 31/5517* (2013.01); *A61K 9/143* (2013.01); *A61K 9/1641* (2013.01); *A61K 9/2059* (2013.01); *A61K 9/204* (2013.01); *A61K 9/1652* (2013.01); *A61K 9/146* (2013.01); *A61K 9/2054* (2013.01); *A61K 9/2018* (2013.01)
USPC ........................................................ 514/220

(58) Field of Classification Search
CPC ...................................................... A61K 9/146
USPC ........................................................ 514/220
See application file for complete search history.

(56) References Cited

U.S. PATENT DOCUMENTS

| | | | |
|---|---|---|---|
| 5,128,142 A * | 7/1992 | Mulligan et al. ............... | 424/457 |
| 5,264,446 A | 11/1993 | Hegasy et al. | |
| 5,712,274 A | 1/1998 | Sueoka et al. | |
| 6,245,356 B1 | 6/2001 | Baichwal | |

FOREIGN PATENT DOCUMENTS

| | | |
|---|---|---|
| EP | 0 671 167 | 9/1995 |
| EP | 0 754 452 | 1/1997 |
| EP | 0 989 131 | 3/2000 |
| GB | 2 119 784 | 11/1983 |
| JP | 56-110612 | 9/1981 |
| JP | 58-183615 | 10/1983 |
| JP | 59-14446 | 4/1984 |
| JP | 7-324086 | 12/1995 |
| JP | 8-143476 | 6/1996 |
| WO | 96/36322 | 11/1996 |
| WO | 98/11111 | 3/1998 |

OTHER PUBLICATIONS

A. P. Simonelli, et al.; "Dissolution Rates of High Energy Polyvinylpyrrolidone (PVP)-Sulfathiazole Coprecipitates"; 1969; Journal of Pharmaceutical Sciences; vol. 58, No. 5, pp. 538-549.
H. Sekikawa et al.; "Dissolution Mechanisms of Drug-Polyvinylpyrrolidone Coprecipitates in Aqueous Solution"; 1979; Chemical and Pharmaceutical Bulletin; vol. 27, No. 5; pp. 1223-1230.
Chiou et al., "Pharmaceutical Application of Solid Dispersion System", Journal of Pharmaceutical Sciences, vol. 60, No. 9, pp. 1281-1302, 1971.
Japanese Notice of Reasons for Refusal (with English translation) issued Aug. 9, 2011 in corresponding Japanese Application No. 2002-510090.

* cited by examiner

*Primary Examiner* — Jake Vu
(74) *Attorney, Agent, or Firm* — Wenderoth, Lind & Ponack, L.L.P.

(57) ABSTRACT

The present invention provides a composition controlling a pH range of release and/or a release rate, which contains (i) a thienotriazolodiazepine compound of the formula (I)

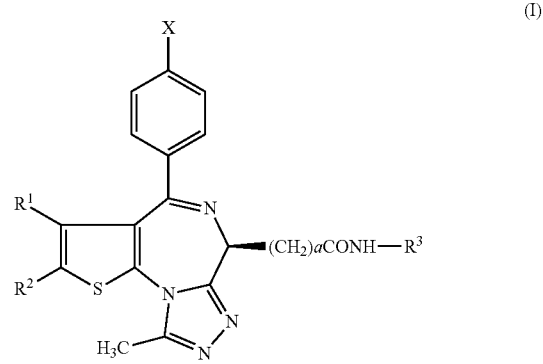

and (ii) at least one kind of ingredient selected from the group consisting of a water-soluble polymer, an enteric polymer, a water-insoluble polymer and a porous polymer and/or a surfactant, as well as a production method thereof.

13 Claims, 4 Drawing Sheets

COMPOSITIONS CONTROLLING PH RANGE OF RELEASE AND/OR RELEASE RATE

This application is a Divisional of U.S. application Ser. No. 12/222,213, filed Aug. 5, 2008 now abandoned, which is a Continuation of U.S. application Ser. No. 10/319,568, filed Dec. 16, 2002 now abandoned, which is a Continuation-in-Part of International application No. PCT/JP01/05151, filed on Jun. 15, 2001.

TECHNICAL FIELD OF THE INVENTION

The present invention relates to a composition that controls a pH range of release and/or a release rate and maximally elicits a therapeutic effect on inflammatory bowel diseases such as ulcerative colitis, Crohn's disease and the like.

BACKGROUND OF THE INVENTION

A compound of the formula (I)

wherein X is a halogen, $R^1$ is C1-C4 alkyl, $R^2$ is C1-C4 alkyl, a is an integer of 1-4, $R^3$ is C1-C4 alkyl, C1-C4 hydroxyalkyl, C1-C4 alkoxy, phenyl optionally having substituent(s) or heteroaryl optionally having substituent(s) (hereinafter sometimes to be also referred to as the present compound) is useful as a therapeutic agent for ulcerative colitis and Crohn's disease (WO98/11111).

Inflammatory bowel disease is an intractable bowel disease that is developed in a neutral area of from the upper small intestine to large intestine. Particularly, Crohn's disease is observed from duodenum to small intestine, and ulcerative colitis occurs in large intestine at lower gastrointestinal tract. The present inventors found through various experiments including animal tests that, in these diseases, drug release (compound of the formula (I)) in a lesion and a direct action thereof on the inflammatory lesion are more important than the absorption of the drug into circulation from the gastrointestinal tract.

However, the present compound is a poorly soluble compound, which shows markedly low solubility particularly in the neutral area, and an extremely high dose is problematically necessary for eliciting the effect of the present compound in a conventional oral preparation. Therefore, for the effect of the present compound to be maximally provided at a low dose, dissolution rate of the drug in the neutral area should be increased and the drug needs to be released in the lesion.

While WO98/11111 discloses, as a preparation for oral administration of the present compound, a composition comprising a mixture of the present compound and additives such as sucrose, lactose, crystalline cellulose, methylcellulose, a synthetic or semi synthetic polymer, and the like, a preparation that achieves the above-mentioned objects cannot be obtained by merely admixing the present compound with such additives, because the present compound is poorly soluble.

In general, dissolution property of a poorly soluble drug is known to be improved by methods such as preparation of the drug in a fine powder, formation of a solvate, increase of surface area by adsorption to the surface of a solid, changing the crystal form (polymorphism), mixing with excipients and pulverizing the mixture, solid dispersion and the like (JP-B-59-14446, JP-A-58-183615 and the like). For example, dissolution property and the like of Griseofulvin have been improved by giving a solid dispersion by dispersing Griseofulvin in polyethylene glycol polymers, which are water-soluble polymers (J. Pharm. Sci., 60(9), 1281-1302 (1971)). In addition, a solid dispersion of polyvinylpyrrolidone and sulfathiazole (J. Pharm. Sci., 58(5), 538-549 (1969)), a solid dispersion of fisoxazole or sulfamethizole and polyvinylpyrrolidone (Chem. Pharm. Bull., 27(5), 1223-1230 (1979)), and the like have been reported. These prior art techniques aim at improving dissolution property and enhancing bioavailability.

Pharmaceutical products are required to have ensured efficacy and safety, as well as various properties satisfying the object of use. Among others, there is a high demand on a system (called DDS) for delivering a necessary amount of a drug to the objective site over a necessary period of time by suitably designing the dosage form. The invention at this time mainly aims at controlling the drug release rate from a composition, thereby to efficiently treat inflammatory bowel diseases.

SUMMARY OF THE INVENTION

The present inventors have conducted intensive studies in an attempt to develop a solid preparation that can be administered orally, by improving the dissolution property of the compound of the formula (I) in the neutral area in the gastrointestinal tract lumen and controlling the release rate. As a result, the present inventors have found that the dissolution property of the present compound in the neutral area can be improved and the release rate of a drug can be designedly controlled by dispersing the present compound in polymer(s), which resulted in the completion of a composition capable of maximally eliciting a therapeutic effect on the inflammatory bowel diseases.

Accordingly, the present invention provides the following.
(1) A composition controlling a pH range of release and/or a release rate, which comprises (i) a thienotriazolodiazepine compound of the formula (I)

wherein X is a halogen, $R^1$ is C1-C4 alkyl, $R^2$ is C1-C4 alkyl, a is an integer of 1-4, $R^3$ is C1-C4 alkyl, C1-C4 hydroxyalkyl, C1-C4 alkoxy, phenyl optionally having substituent(s), or heteroaryl optionally having substituent(s), a pharmaceutically acceptable salt thereof or a hydrate thereof; and (ii) at least one kind of ingredient selected from the group consisting of a water-soluble polymer, an enteric polymer, a water-insoluble polymer and a porous polymer.

(2) The composition controlling a pH range of release and/or a release rate of (1), wherein the ingredient is at least one kind selected from the group consisting of an enteric polymer and a water-insoluble polymer.

(3) The composition controlling a pH range of release and/or a release rate of (1), which further comprises a surfactant.

(4) The composition controlling a pH range of release and/or a release rate of (1), wherein the compound of the formula (I) is (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide.

(5) The composition controlling a pH range of release and/or a release rate of (1), which is a therapeutic agent for an inflammatory disease in the neutral area in the gastrointestinal tract lumen.

(6) The composition controlling a pH range of release and/or a release rate of (5), wherein the inflammatory disease is ulcerative colitis or Crohn's disease.

(7) The composition controlling a pH range of release and/or a release rate of (1), which is a solid dispersion.

(8) A composition controlling a pH range of release and/or a release rate, which comprises the compound of the formula (I), a pharmaceutically acceptable salt thereof or a hydrate thereof, and a surfactant.

(9) The composition controlling a pH range of release and/or a release rate of (8), wherein the compound of the formula (I) is (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide.

(10) The composition controlling a pH range of release and/or a release rate of (8), which is a therapeutic agent for an inflammatory disease in the neutral area in the gastrointestinal tract lumen.

(11) The composition controlling a pH range of release and/or a release rate of (10), wherein the inflammatory disease is ulcerative colitis or Crohn's disease.

(12) The composition controlling a pH range of release and/or a release rate of (8), which is a solid dispersion.

(13) A production method of a composition controlling a pH range of release and/or a release rate, which comprises dissolving or dispersing the compound of the formula (I), a pharmaceutically acceptable salt thereof or a hydrate thereof, and a polymer in a solvent, and evaporating the solvent.

(14) The method of (13), wherein the polymer is at least one kind selected from the group consisting of a water-soluble polymer, an enteric polymer, a water-insoluble polymer and a porous polymer.

(15) The method of (13), wherein the polymer is at least one kind selected from the group consisting of an enteric polymer and a water-insoluble polymer.

(16) The method of (13), further comprising dissolving or dispersing a surfactant in the solvent.

(17) A production method of a composition controlling a pH range of release and/or a release rate, which comprises dissolving or dispersing the compound of the formula (I), a pharmaceutically acceptable salt thereof or a hydrate thereof, and a surfactant in a solvent, and evaporating the solvent.

(18) A composition controlling a pH range of release and/or a release rate, which is obtainable by the method of any of (13) to (17).

(19) The composition controlling a pH range of release and/or a release rate of (18), which is a solid dispersion.

(20) A production method of a composition controlling a pH range of release and/or a release rate, which comprises melting the compound of the formula (I), a pharmaceutically acceptable salt thereof or a hydrate thereof, dissolving or dispersing a polymer, and cooling for solidification.

(21) The method of (20), wherein the polymer is at least one kind selected from the group consisting of a water-soluble polymer, an enteric polymer, a water-insoluble polymer and a porous polymer.

(22) The method of (20), wherein the polymer is at least one kind selected from the group consisting of an enteric polymer and a water-insoluble polymer.

(23) The method of (20), further comprising dissolving or dispersing a surfactant in the melt product.

(24) A production method of a composition controlling a pH range of release and/or a release rate, which comprises melting the compound of the formula (I), a pharmaceutically acceptable salt thereof or a hydrate thereof, dissolving or dispersing a surfactant, and cooling for solidification.

(25) A composition controlling a pH range of release and/or a release rate which is obtainable by the method of any of (20)-(24).

(26) The composition controlling a pH range of release and/or a release rate of (25), which is a solid dispersion.

DETAILED DESCRIPTION OF THE INVENTION

The "composition controlling a pH range of release and/or a release rate" of the present invention is provided as a solid dispersion of a compound represented by the formula (I), a pharmaceutically acceptable salt thereof or a hydrate thereof (i.e., the present compound) dispersed in polymer(s), with which to realize improvement in dissolution property of the present compound in the neutral area and free control of a release rate thereof.

In the present invention, by the "controlling a pH range of release" is meant that the dissolution rate of the present compound in the neutral pH range, i.e., about pH 5-about pH 9, is significantly improved as compared to the dissolution rates of the dosage forms other than that of the present invention, and that the dissolution rate is preferably controlled so that the present compound will not substantially dissolve out in the acidic pH range, or not more than about pH 4. As used herein, by the "not substantially dissolve" is meant that the drug does not dissolve out to the degree therapeutic efficiency is impaired.

In the present invention, by the "controlling release rate" is meant that the release rate of the present compound from a preparation can be controlled freely, and can be designed as necessary to release nearly 100% of the present compound in a short period of time or gradually in a sustained manner.

Examples of each group of the formula (I) are as follows. The halogen for X is chlorine, bromine, fluorine or iodine, with preference given to chlorine.

The C1-C4 alkyl for $R^1$, $R^2$ and $R^3$ is methyl, ethyl, propyl, isopropyl, butyl, isobutyl, secondary butyl and tertiary butyl, with preference given to methyl.

The C1-C4 hydroxyalkyl for $R^3$ is hydroxymethyl, 2-hydroxyethyl, 1-hydroxyethyl, 3-hydroxypropyl, 4-hydroxybutyl and the like.

The C1-C4 alkoxy for $R^3$ is methoxy, ethoxy, n-propoxy, isopropoxy, n-butoxy, isobutoxy and the like.

The phenyl optionally having substituent(s) for $R^3$ is phenyl which may have 1 or 2 substituents from halogens (chlorine, bromine, fluorine and the like), C1-C4 alkyl (methyl, ethyl and the like), hydroxy, C1-C4 hydroxyalkyl (hydroxymethyl, hydroxyethyl and the like), amino and nitro, and is exemplified by 4-hydroxyphenyl, 4-aminophenyl, 3-chlorophenyl and the like.

The heteroaryl optionally having substituent(s) for $R^3$ is pyridyl, pyrazinyl, pyrimidinyl, thienyl, furyl and the like, which may have 1 or 2 substituents from halogen (chlorine, bromine, fluorine and the like), C1-C4 alkyl (methyl, ethyl and the like), hydroxy, amino, nitro and C1-C4 alkoxy (methoxy, ethoxy and the like), and is exemplified by 3-pyridyl, 2-methoxy-3-pyridyl, 4-methoxy-3-pyridyl and the like.

The pharmaceutically acceptable salt of the present compound includes, for example, acid addition salts with inorganic acid (hydrochloric acid, hydrobromic acid, sulfuric acid, phosphoric acid, nitric acid and the like) or organic acid (acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, ascorbic acid and the like), and salts with inorganic base (sodium hydroxide, potassium hydroxide, calcium hydroxide, magnesium hydroxide, zinc hydroxide, ammonium hydroxide and the like), organic base (methylamine, diethylamine, triethylamine, dicyclohexylamine, triethanolamine, ethylenediamine, tris-hydroxymethylaminomethane, quinine, guanidine, cinchonine and the like) or amino acid (lysin, ornithine, arginine, alanine and the like). In view of the object of the present invention, the salt is preferably non-toxic. In addition, hydrate (monohydrate, dihydrate and the like) and other solvates are included.

The compound of the formula (I) includes
(1) (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide,
(2) (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide dihydrate,
(3) (S)-2-[4-(4-chlorophenyl)-2,3,9-trimethyl-6H-thieno[3,2-f][1,2,4]triazolo[4,3-a][1,4]diazepin-6-yl]-N-methylacetamide 1/4 hydrate,
(4) (S)-2-[4-(4-chlorophenyl)-2,3,9-trimethyl-6H-thieno[3,2-f][1,2,4]triazolo[4,3-a][1,4]diazepin-6-yl]-N-(2-hydroxyethyl)acetamide 1/4 hydrate,
(5) (S)-N-(4-aminophenyl)-2-[4-(4-chlorophenyl)-2,3,9-trimethyl-6H-thieno[3,2-f][1,2,4]triazolo[4,3-a][1,4]diazepin-6-yl]acetamide,
(6) (S)-2-[4-(4-chlorophenyl)-2,3,9-trimethyl-6H-thieno[3,2-f][1,2,4]triazolo[4,3-a][1,4]diazepin-6-yl]-N-(3-pyridyl)acetamide hydrochloride,
(7) (S)-2-[4-(4-chlorophenyl)-2,3,9-trimethyl-6H-thieno[3,2-f][1,2,4]triazolo[4,3-a][1,4]diazepin-6-yl]-N-(2-methoxy-3-pyridyl)acetamide,
(8) (S)-2-[4-(4-chlorophenyl)-2,3,9-trimethyl-6H-thieno[3,2-f][1,2,4]triazolo[4,3-a][1,4]diazepin-6-yl]-N-(4-methoxy-3-pyridyl)acetamide,
(9) (S)-2-[4-(4-chlorophenyl)-2,3,9-trimethyl-6H-thieno[3,2-f][1,2,4]triazolo[4,3-a][1,4]diazepin-6-yl]-N-methoxyacetamide 1/4 hydrate, and the like.

The compound of the formula (I) is preferably (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide, particularly, dihydrate thereof is most preferable from the aspect of stability.

The compound of the formula (I) can be produced according to the method described in WO98/11111.

The composition of the present invention can be produced by dissolving or dispersing the present compound and polymer(s) and/or a surfactant in a suitable organic solvent, and then drying and evaporating the organic solvent under reduced pressure or atmospheric pressure according to a conventional method (dissolution method). Alternatively, the present compound is melted by heating to a temperature above the melting point, then polymer(s) and/or a surfactant is/are dissolved or dispersed therein, and the mixture is rapidly cooled to produce the composition (melting method).

The "polymer" to be used in the present invention is not particularly limited as long as it can be combined with the present compound to improve dissolution property and enable control of the release rate of the present compound in a neutral area. Preferably, it is an enteric polymer, a water-insoluble polymer, a porous polymer or a water-soluble polymer, and more preferably an enteric polymer or a water-insoluble polymer from the aspect of increases a dissolution rate of a drug in the neutral area of from the small intestine to the large intestine at a lower gastrointestinal tract, and provision of a composition that releases the drug in a lesion. For example, the following polymers can be mentioned.

As the enteric polymers, hydroxypropylmethylcellulose phthalate 220824 (HP50), hydroxypropylmethylcellulose phthalate 220731 (HP55), hydroxypropylmethylcellulose acetate succinate, carboxymethylethylcellulose, cellulose acetate phthalate, methacrylic acid-ethyl acrylate copolymer, methacrylic acid-methyl methacrylate copolymer and the like are exemplified, with preference given to hydroxypropylmethylcellulose phthalate 220824 (HP50), hydroxypropylmethylcellulose phthalate 220731 (HP55), methacrylic acid-methyl methacrylate copolymer.

As the water-soluble polymer, polyvinylpyrrolidone, polyvinyl alcohol, methylcellulose, hydroxypropylcellulose, hydroxypropylmethylcellulose 2208 (Metolose 90SH), hydroxypropylmethylcellulose 2906 (Metolose 65SH), hydroxypropylmethylcellulose 2910 (Metolose 60SH), carboxymethylethylcellulose, pullulan, dextrin, sodium alginate, aminoalkyl methacrylate copolymer E, polyvinylacetal diethylaminoacetate and the like are exemplified. Preferred are polyvinylpyrrolidone, hydroxypropylmethylcellulose, carboxymethylethylcellulose, methylcellulose and hydroxypropylcellulose.

As the water-insoluble polymer, ethylcellulose, ethyl acrylate-methyl methacrylate-trimethylammonioethyl methacrylate chloride copolymer, methacrylic acid-ethyl acrylate copolymer, methacrylic acid-methyl methacrylate copolymer, carboxymethylcellulose sodium (carmellose sodium), low substituted hydroxypropylcellulose, croscarmellose sodium, crospovidone, Acacia, tragacanth, propylene glycol alginate, agar powder, gelatin, starch, partly pregelatinized starch, oil, phospholipid (lecithin), glucomannans and the like are exemplified. Preferably, methacrylic acid-ethyl acrylate copolymer, ethylcellulose, ethyl acrylate-methyl methacrylate-trimethylammonioethyl methacrylate chloride copolymer are exemplified.

As the porous polymers, magnesium aluminometasilicate, dimagnesium aluminosilicate, magnesium bismuth aluminosilicate, hydrotalcite, aluminum silicate, dried aluminum hydroxide gel, magnesium oxide, light anhydrous silicic acid and special calcium silicate and the like are exemplified. Preferably, light anhydrous silicic acid, special calcium silicate and magnesium aluminometasilicate are exemplified.

The above-mentioned respective polymers can be used alone or, where necessary, two or more kinds thereof may be mixed for use.

The proportion of the present compound and polymer(s) to be mixed is not particularly limited, as long as it can improve dissolution property of the present compound in a neutral area and varies depending on the kind of polymer, object of use, properties of the membrane and the like. Generally, 0.1-999, preferably 0.2-500, more preferably 0.5-50 of polymer is suitable relative to the present compound as 1.

In addition, it is possible to combine the above-mentioned polymer(s) with a surfactant. By a combined use with a surfactant, the release rate of the present compound can be increased. The surfactant to be used in the present invention is, for example, polysorbate (40, 60, 65, 80), sodium lauryl sulfate, hydrogenated castor oil, polyoxyethylene hydrogenated castor oil and the like. Preferably, polyoxyethylene hydrogenated castor oil is used.

The release rate of the present compound from the composition of the present invention can be controlled by combining polymers and surfactants, adjusting the mixing ratio of the present compound with them, and the like. Those of ordinary skill in the art can easily determine preferable polymers and surfactants and mixing ratios thereof, and the like depending on the object of use. For example, when the present compound should be topically effective from around the duodenum to the upper small intestine, the combined use of a surfactant affords nearly 100% dissolution rate in a short time. Conversely, when sustained release of a drug over from small intestine to large intestine is desired, an easy control is afforded by combining a water-insoluble molecule as a polymer, or increasing/decreasing the amount of the polymer to be added relative to the present compound.

The composition of the present invention can be prepared as a composition containing the present compound and a surfactant. The surfactant improves dissolution property and dissolution rate of the present compound in a neutral pH range. In this case, dissolution in an acidic pH range is suppressed by using the composition in the form of an enteric preparation having a sustained release coating (ethylcellulose, ethyl acrylate-methyl methacrylate-trimethylammonioethyl methacrylate chloride copolymer and the like) or an enteric coating (hydroxypropylmethylcellulose phthalate (HP55), methacrylic acid-methyl methacrylate copolymer and the like).

When an organic solvent is used for the production of the composition of the present invention, it is free of any limitation as long as it dissolves the present compound and does not show an adverse influence on the properties of the polymers and surfactants to "control a pH range of release and/or a release rate of the present compound". For example, ethanol, acetone, dichloromethane and the like are used.

While the operation conditions of the dissolution method such as treatment temperature, treatment time and the like vary depending on the compound to be used, solvent and the like, the conditions of generally from room temperature to 200° C. for several minutes to several dozen hours are employed.

In contrast, when the composition of the present invention is to be produced by the melting method, the polymer and surfactant to be used should be able to maintain the properties of "controlling a pH range of release and/or a release rate of the present compound" at the melting point of the present compound.

For the composition of the present invention obtained as above, it is important that the present compound does not have a crystalline structure in a polymer or a surfactant and that the present compound is present at a molecular level in a polymer or a surfactant, whereby the dissolution property of the present compound can be improved.

A solid dispersion of the present compound, which is obtained as mentioned above, can be used as it is, but may be formulated into various dosage forms generally known as preparation for oral administration, such as fine granules, granules, tablets, capsules and the like, by a known production method. Where necessary, suitable additives such as coloring agent, corrigent, excipient (e.g., lactose, sucrose, starch, crystalline cellulose and the like), disintegrant (e.g., low substituted hydroxypropylcellulose, croscarmellose sodium, crospovidone, sodium carboxymethyl starch and the like), lubricant (e.g., magnesium stearate and the like), plasticizer (triethyl citrate, polyethylene glycol and the like), pH adjusting agent (citric acid, ascorbic acid, magnesium aluminometasilicate etc.) and the like can be added. These additives may be added to an organic solvent (or melted present compound) or a solid dispersion of the present compound.

The composition of the present invention is useful as an oral administration preparation for the treatment of inflammatory disease in the neutral area in the gastrointestinal tract lumen, or an area of from the upper small intestine to the large intestine, because dissolution rate of the present compound in the neutral area can be improved and the present compound is not substantially dissolved in an acidic area (therefore dissolution of the present compound in the stomach upon oral administration can be avoided). Particularly, the composition of the present invention can be effectively used for the treatment of inflammatory bowel diseases such as ulcerative colitis, Crohn's disease and the like, that are noticeably seen in such areas.

While the dose of the oral preparation of the present invention varies depending on the kind and severity of the disease, drug sensitivity, body weight and age of patients, and the like, they are generally about 0.1-about 10 mg/kg in the amount of the present compound for an adult per day, and this dose can be administered once or divided in several doses.

The present invention is now explained in detail by referring to Examples, Control Examples and Experimental Examples, which are not to be construed as limitative. In the following Experimental Examples, (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide dihydrate was used as the present compound. In the following, this compound is referred to as "Compound A".

EXAMPLE 1

Compound A (1.074 g, 1 g by conversion to anhydride) and polyvinylpyrrolidone (1 g or 5 g, product name, Kolidon;

manufactured by BASF) were dissolved in ethanol and the organic solvent was evaporated under reduced pressure using a rotary evaporator. The obtained solid was pulverized to give fine granules (a) or (b).
- (a) - - - compound A:polyvinylpyrrolidone=1:1
- (b) - - - compound A:polyvinylpyrrolidone=1:5

EXAMPLE 2

Compound A (1.074 g, 1 g by conversion to anhydride) and polyoxyethylene hydrogenated castor oil (5 g, product name, HCO-60; manufactured by Nihon Surfactant Kogyo K.K.) were dissolved in ethanol and the mixture was adsorbed to special calcium silicate (1 g, product name, FLORITE RE; manufactured by Eisai Co., Ltd.) to give a powder.

EXAMPLE 3

Compound A (1.074 g, 1 g by conversion to anhydride) was dissolved in ethanol and the mixture was adsorbed to special calcium silicate (1 g, product name, FLORITE RE; manufactured by Eisai Co., Ltd.) to give a powder.

EXAMPLE 4

Compound A (13.5 g) and hydroxypropylmethylcellulose phthalate 200731 (37.5 g, product name, HP-55; manufactured by Shin-Etsu Chemical Co., Ltd.) were dissolved in a mixture of ethanol and acetone. The mixture was granulated in an agitating granulator with lactose (51.5 g), corn starch (29.25 g) and crystalline cellulose (60.0 g). Low substituted hydroxypropylcellulose (60 g, product name, L-HPC; manufactured by Shin-Etsu Chemical Co., Ltd.) and magnesium stearate (1.5 g) were mixed, and then the mixture was tableted using a tableting machine to give tablets having a diameter of 7.0 mm and weighing 120 mg.

EXAMPLE 5

Compound A (25 g), ethyl acrylate-methyl methacrylate-trimethylammonioethyl methacrylate chloride copolymer (20 g, Eudragit RS, manufactured by Röhm), methacrylic acid-methyl methacrylate copolymer (80 g, Eudragit L100-55, manufactured by Röhm), triethyl citrate (12.5 g, CITROFLEX 2, SC-60, CYUGAI BOUEKI), magnesium aluminometasilicate (25 g, Neusilin $FH_2$, manufactured by Fuji Chemical Industry Co., Ltd.) and talc (350 g) were dissolved and/or dispersed in a mixture of water and ethanol. The mixture was applied to sucrose-starch sphere (250 g, Nonpareil 101, FREUND Inc.) using a centrifugal fluidized bed granulator to give granules.

EXAMPLE 6

Compound A (2.0 g), ethyl acrylate-methyl methacrylate-trimethylammonioethyl methacrylate chloride copolymer (1.8 g, Eudragit RS, manufactured by Röhm), methacrylic acid-methyl methacrylate copolymer (4.2 g, Eudragit L100-55, manufactured by Röhm) and talc (18.0 g) were dissolved and/or dispersed in a mixture of water and ethanol, and spray-dried in a centrifugal fluidized bed granulator to give a powder.

CONTROL EXAMPLE 1

Compound A (1 g) and lactose (9 g) were mixed in a mortar to give a 10% powder mixture.

CONTROL EXAMPLE 2

Ethyl acrylate-methyl methacrylate-trimethylammonioethyl methacrylate chloride copolymer (1.8 g, Eudragit RS, manufactured by Röhm), methacrylic acid-methyl methacrylate copolymer (4.2 g, Eudragit L100-55, manufactured by Röhm) and talc (18.0 g) were dissolved and/or dispersed in a mixture of water and ethanol, and spray-dried in a centrifugal fluidized bed granulator to give a placebo powder. The placebo powder (24.0 g) was mixed with Compound A (2.0 g) to give a powder of a physical mixture of Compound A.

EXPERIMENTAL EXAMPLE 1

Dissolution Test

Figure 1:
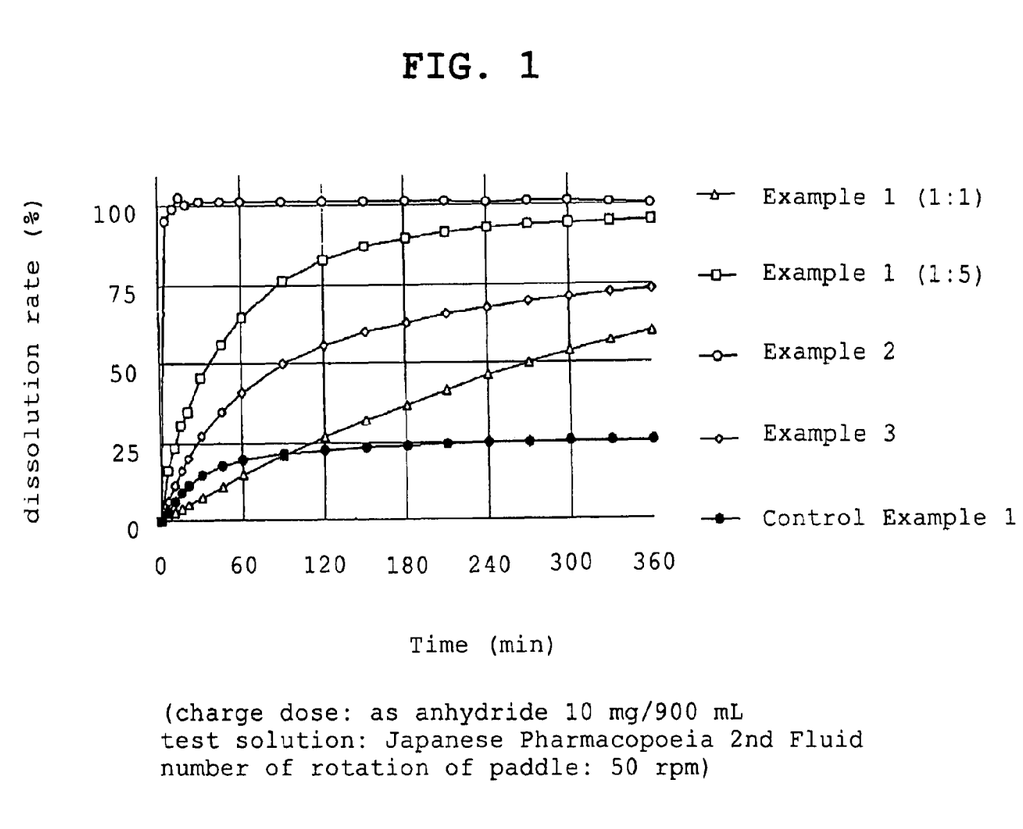
FIG. 1 shows dissolution behaviors of the compositions controlling a pH range of release and a release rate according to the present invention (Examples 1-3) and Control Example 1 in Japanese Pharmacopoeia 2nd Fluid.

The dissolution property of Compound A contained in the compositions obtained in Examples 1-3 and the powder mixture obtained in Control Example 1 was evaluated in Japanese Pharmacopoeia 2nd Fluid (pH 6.8) according to a conventional method. That is, each sample of Examples 1-3 and Control Example 1 (in the corresponding amount containing 10 mg of compound A) was added to Japanese Pharmacopoeia 2nd Fluid (900 mL) and dissolution test solution was taken with time at 37° C. Using a Fine Filter (pore size 5 µm: manufactured by Toyama Sangyo Co., Ltd.), the test solution was filtrated and the amount of compound A dissolved in the filtrate was measured with a spectrophotometer. The results are shown in FIG. 1.

As a result, the dissolution rate was 25% in Control Example 1 even after 360 min. In contrast, a dissolution rate of not less than 50% was achieved even after 360 min by combination with a polymer. From the results of Example 1, it was clarified that an increased mixing ratio of the polymer resulted in a higher release rate, and from the comparison of Examples 2 and 3, it was clarified that the addition of a surfactant, polyoxyethylene hydrogenated castor oil, derived 100% release of the drug within 30 min.

EXPERIMENTAL EXAMPLE 2

Dissolution Test

The dissolution property of the compositions obtained in Examples 4 and 5 was evaluated in Japanese Pharmacopoeia 1st Fluid (pH 1.2) and 2nd Fluid (pH 6.8) according to a conventional method. That is, each sample of Examples 4 and 5 (in the corresponding amount containing 5 mg of compound A) was added to the dissolution test solution (900 mL). The dissolution test solution was taken with time at 37° C. Using a Fine Filter (pore size 5 µm: manufactured by Toyama Sangyo Co., Ltd.), the test solution was filtrated and the amount of compound A dissolved in the filtrate was measured with a spectrophotometer. The results are shown in FIGS. 2 and 3.

Figure 2:
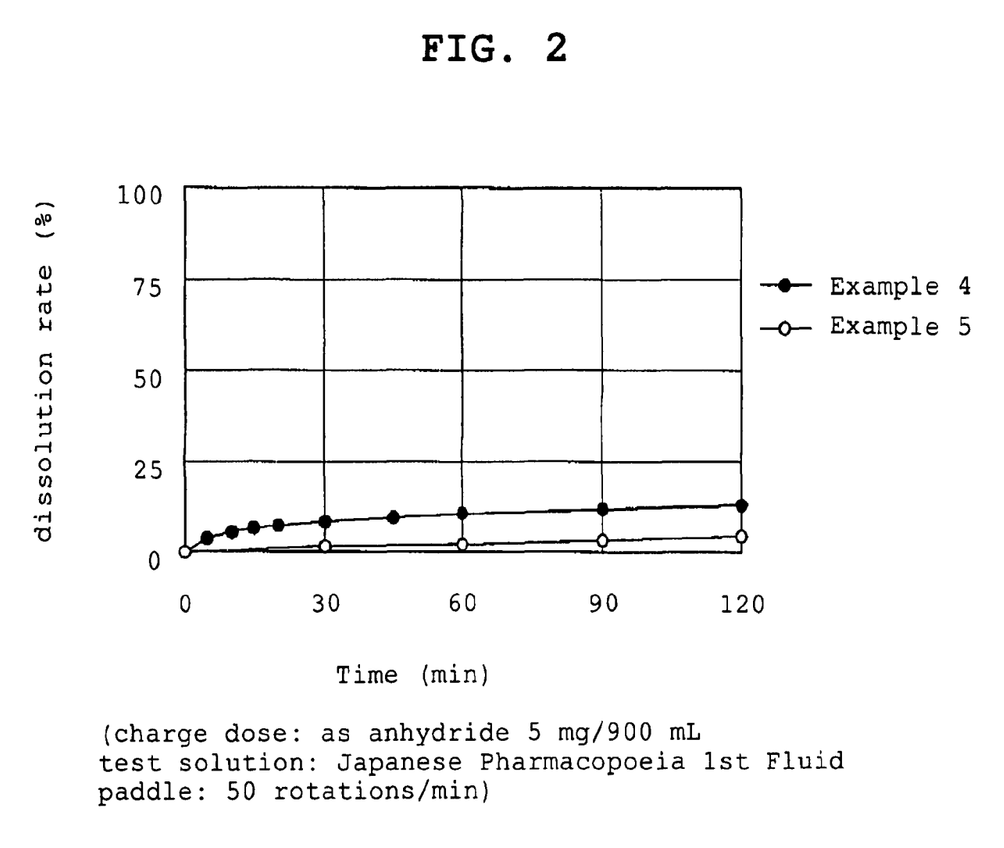
FIG. 2 shows dissolution behaviors of the compositions controlling a pH range of release and a release rate according to the present invention (Examples 4, 5) in Japanese Pharmacopoeia 1st Fluid.
Figure 3:
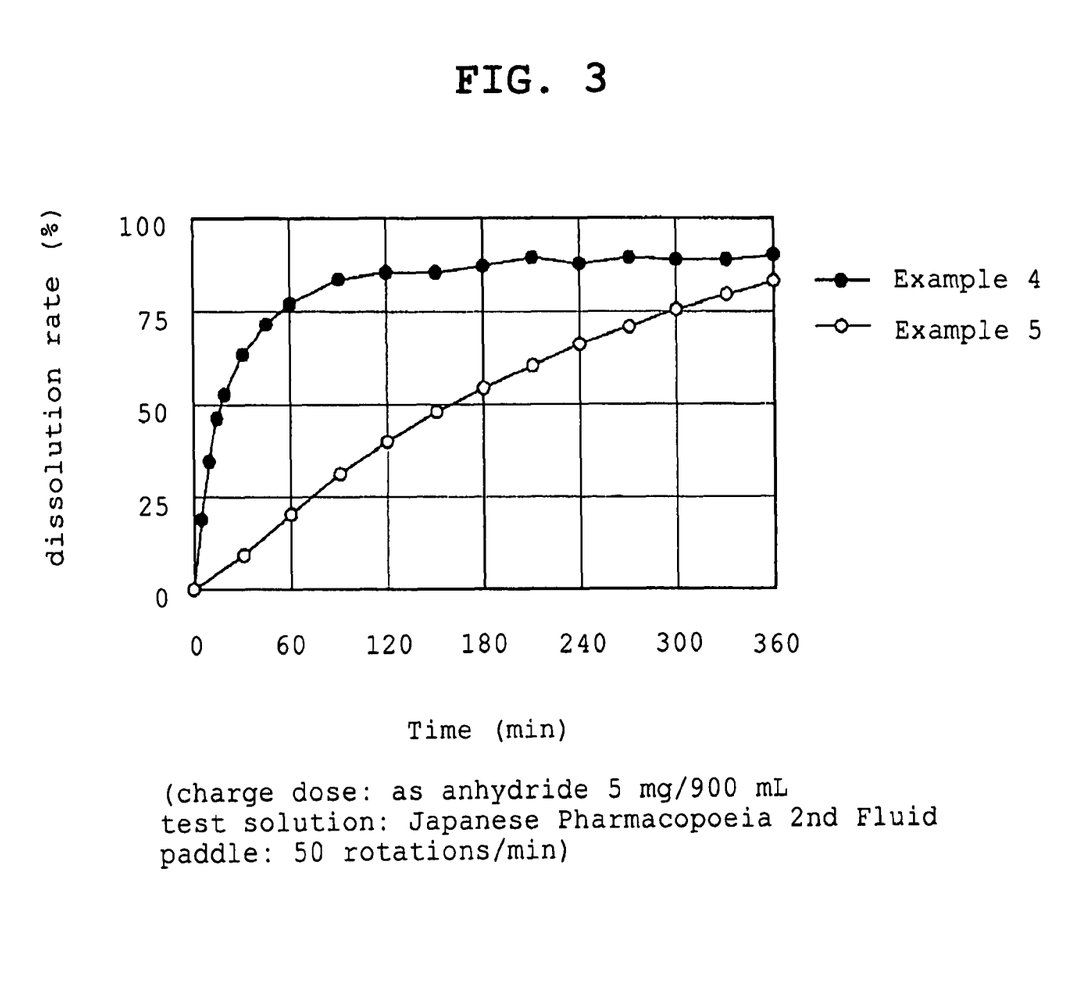
FIG. 3 is shows dissolution behaviors of the compositions controlling a pH range of release and a release rate according to the present invention (Examples 4, 5) in Japanese Pharmacopoeia 2nd Fluid.

As the results of FIG. 2 show, Examples 4 and 5 were found to have been free of dissolution in the pH 1.2 solution. This means that the drug is designed to scarcely dissolve out in the stomach that does not show inflammatory diseases. In contrast, as shown in FIG. 3, the drug gradually dissolved in the pH 6.8 solution and the dissolution rate of not less than 75% was achieved after 360 min.

EXPERIMENTAL EXAMPLE 3

Dissolution Test

Figure 4:
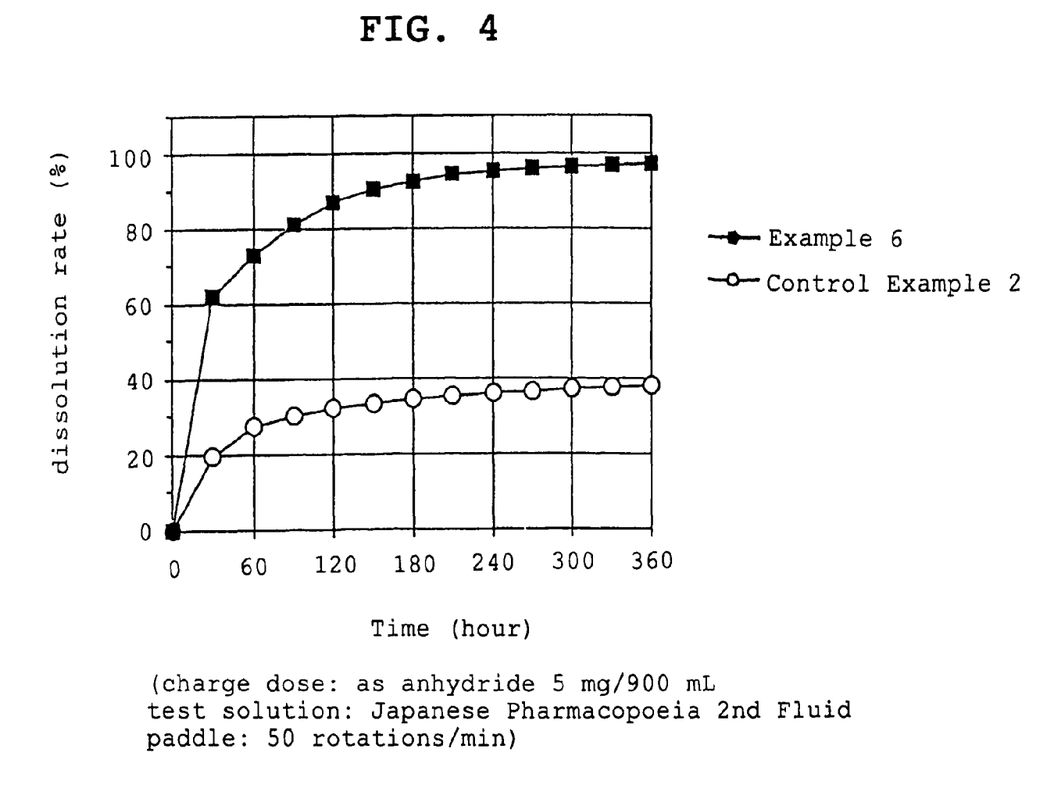
FIG. 4 shows dissolution behaviors of the compositions controlling a pH range of release and a release rate according to the present invention (Examples 6) and Control Example 2 in Japanese Pharmacopoeia 2nd Fluid.

The dissolution property of Compound A contained in the composition (solid dispersion) obtained in Example 6 and in the composition (physical mixture) obtained in Control Example 2 was evaluated in Japanese Pharmacopoeia 2nd Fluid (pH 6.8) according to a conventional method. That is, each sample of Example 6 and Control Example 2 (in the corresponding amount containing 5 mg of compound A) was added to Japanese Pharmacopoeia 2nd Fluid (900 mL) and dissolution test solution was taken with time at 37° C. The amount of compound A dissolved in the filtrate was measured with a spectrophotometer. The results are shown in FIG. 4.

As a result, the dissolution rate was about 37% even after 360 min in Control Example 2. In contrast, the powder of Example 6 obtained by dissolution and solidification along with acrylic polymers achieved a dissolution rate of up to 97% 360 min later. The difference between them is attributable to the fact that the composition obtained in Example 6 was a solid dispersion.

EXPERIMENTAL EXAMPLE 4

Therapeutic Effect in TNBS-induced Rat Enteritis Model

The efficacy of each sample of Examples 1-3 and Control Example 1 (in the corresponding amount containing 10 mg of compound A) was confirmed using trinitrobenzenesulfonic acid (TNBS)-induced rat enteritis models (n=7-8) widely used as experimental animal models of inflammatory bowel disease. That is, according to a conventional method, TNBS was injected at 7 cm from the rat anus to onset the enteritis. The anti-inflammatory effect was evaluated by measuring the myeloperoxidase (MPO) activity which is an index of infiltration of leukocytes into the inflammatory lesion. The analysis to evaluate statistical difference relative to TNBS alone administration group was conducted by the Dunnett Method.

TABLE 1

MPO activity by rectal administration

| preparation | dose (mg/kg) | MPO activity (U/ml) mean ± SE | statistical difference |
|---|---|---|---|
| TNBS alone group | — | 0.247 ± 0.004 | control group |
| Example 1 (1:1) | 0.03 | 0.176 ± 0.002 | P < 0.01 |
|  | 0.1 | 0.147 ± 0.004 | P < 0.01 |
|  | 0.3 | 0.140 ± 0.004 | P < 0.01 |
| Example 1 (1:5) | 0.03 | 0.150 ± 0.005 | P < 0.01 |
|  | 0.1 | 0.145 ± 0.003 | P < 0.01 |
|  | 0.3 | 0.136 ± 0.005 | P < 0.01 |
| TNBS alone group | — | 0.310 ± 0.013 | control group |
| Example 2 | 0.03 | 0.168 ± 0.007 | P < 0.01 |
|  | 0.1 | 0.153 ± 0.003 | P < 0.01 |
|  | 0.3 | 0.153 ± 0.002 | P < 0.01 |
| Example 3 | 0.03 | 0.181 ± 0.011 | P < 0.01 |
|  | 0.1 | 0.167 ± 0.002 | P < 0.01 |
|  | 0.3 | 0.144 ± 0.005 | P < 0.01 |
| TNBS alone group | — | 0.275 ± 0.011 | control group |
| Control Example 1 | 0.3 | 0.182 ± 0.005 | P < 0.01 |
|  | 1 | 0.154 ± 0.004 | P < 0.01 |
|  | 3 | 0.142 ± 0.003 | P < 0.01 |

As a result of administration near inflammatory lesion (enteral administration), the compositions of Examples 1-3 for controlling a pH range of release and a release rate, which show improved solubility as compared to Control Example 1, significantly suppressed increase of activity of MPO with about 1/10 of the dose of Control Example 1. An influence due to difference in the release rate of Examples 1-3 was not found (Table 1).

In the Table, the ratio of preparation of Example 1 is the mixing ratio of the Compound A and polyvinylpyrrolidone.

TABLE 2

MPO activity by oral administration

| preparation | dose (mg/kg) | MPO activity (U/ml) mean ± SE | statistical difference |
|---|---|---|---|
| TNBS alone group | — | 0.277 ± 0.003 | control group |
| Example 1 (1:1) | 0.03 | 0.200 ± 0.005 | P < 0.01 |
|  | 0.1 | 0.183 ± 0.004 | P < 0.01 |
|  | 0.3 | 0.153 ± 0.007 | P < 0.01 |
| Example 1 (1:5) | 0.03 | 0.221 ± 0.005 | P < 0.01 |
|  | 0.1 | 0.188 ± 0.002 | P < 0.01 |
|  | 0.3 | 0.171 ± 0.003 | P < 0.01 |
| TNBS alone group | — | 0.262 ± 0.008 | control group |
| Example 2 | 0.03 | 0.254 ± 0.006 | NS |
|  | 0.1 | 0.230 ± 0.008 | P < 0.01 |
|  | 0.3 | 0.177 ± 0.009 | P < 0.01 |
| Example 3 | 0.03 | 0.174 ± 0.007 | P < 0.01 |
|  | 0.1 | 0.155 ± 0.004 | P < 0.01 |
|  | 0.3 | 0.146 ± 0.009 | P < 0.01 |
| TNBS alone group | — | 0.281 ± 0.003 | control group |
| Control Example 1 | 0.3 | 0.217 ± 0.006 | P < 0.01 |
|  | 1 | 0.166 ± 0.003 | P < 0.01 |
|  | 3 | 0.146 ± 0.003 | P < 0.01 |

NS: no statistical difference

In contrast, as a result of oral administration, the anti-inflammatory effect of Example 2, which showed the highest dissolution property and highest release rate, was weak as compared to other release rate controlling compositions. By controlling the release rate to a sustained one, the effect was improved (Table 2).

The present invention provides a release control composition capable of designedly controlling the dissolution property and release rate of the compound of the formula (I) in the gastrointestinal tract, by combining the compound and water-soluble polymer, enteric polymer, water-insoluble polymer or porous polymer, and/or surfactant to give a solid dispersion. Using this technique, expression of the maximum anti-inflammatory effect at a low dose has become possible in the target organs having ulcerative colitis and Crohn's disease. Accordingly, the present composition is useful as a preparation for oral administration for the treatment of the above-mentioned diseases.

This application is based on a patent application No. 182293/2000 filed in Japan, the contents of which are hereby all incorporated by reference.

The references cited herein, including patents and patent applications, are hereby incorporated in their entireties by reference, to the extent that they have been disclosed herein.

What is claimed is:

1. A composition controlling a pH range of release and/or a release rate, which comprises
   (i) a thienotriazolodiazepine compound of the formula (I)

(I)

wherein X is a halogen, $R^1$ is C1-C4 alkyl, $R^2$ is C1-C4 alkyl, a is an integer of 1-4, $R^3$ is C1-C4 alkyl, C1-C4 hydroxyalkyl, C1-C4 alkoxy, phenyl optionally having substituent(s), or heteroaryl optionally having substituent(s), a pharmaceutically acceptable salt thereof or a hydrate thereof; and
   (ii) at least one polymer selected from the group consisting of hydroxypropylmethylcellulose phthalate, methacrylic acid-methyl methacrylate copolymer and hydroxypropylmethylcellulose acetate succinate, which is a solid dispersion, and wherein the compound of the formula (I), a pharmaceutically acceptable salt thereof or a hydrate thereof is dispersed in the polymer.

2. The composition of claim 1, which further comprises a surfactant.

3. The composition of claim 1, wherein the compound of the formula (I) is (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide.

4. The composition of claim 3, which is a therapeutic agent for an inflammatory disease in a neutral area in a gastrointestinal tract lumen.

5. The composition of claim 4, wherein the inflammatory disease is ulcerative colitis or Crohn's disease.

6. A production method of the composition of claim 1, which comprises dissolving or dispersing the compound of the formula (I), a pharmaceutically acceptable salt thereof or a hydrate thereof, and the polymer in a solvent, and evaporating the solvent.

7. The method of claim 6, further comprising dissolving or dispersing a surfactant in the solvent.

8. A production method of the composition of claim 1, which comprises melting the compound of the formula (I), a pharmaceutically acceptable salt thereof or a hydrate thereof to give a melt product, dissolving or dispersing the polymer in the melt product, and cooling for solidification.

9. The method of claim 8, further comprising dissolving or dispersing a surfactant in the melt product.

10. A composition controlling a pH range of release and/or a release rate which is obtainable by the method of claim 6.

11. A composition controlling a pH range of release and/or a release rate which is obtainable by the method of claim 8.

12. A method for controlling a pH range of release and/or a release rate of a thienotriazolodiazepine compound of the formula (I)

(I)

wherein X is a halogen, $R^1$ is C1-C4 alkyl, $R^2$ is C1-C4 alkyl, a is an integer of 1-4, $R^3$ is C1-C4 alkyl, C1-C4 hydroxyalkyl, C1-C4 alkoxy, phenyl optionally having substituent(s), or heteroaryl optionally having substituent(s), a pharmaceutically acceptable salt thereof or a hydrate thereof,
   which method comprises administering a composition to a patient,
   wherein the composition comprises
      (i) the compound of the formula (I), a pharmaceutically acceptable salt thereof or a hydrate thereof; and
      (ii) at least one polymer selected from the group consisting of hydroxypropylmethylcellulose phthalate, methacrylic acid-methyl methacrylate copolymer and hydroxypropylmethylcellulose acetate succinate, and is a solid dispersion, and wherein the compound of the formula (I), a pharmaceutically acceptable salt thereof or a hydrate thereof is dispersed in the polymer.

13. The method of claim 12, wherein the compound of the formula (I) is (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide.

* * * * *